United States Patent [19]

Carder et al.

[11] Patent Number: 4,979,396
[45] Date of Patent: Dec. 25, 1990

[54] FATIGUE TESTING APPARATUS

[75] Inventors: James H. Carder; Anh Le, both of Gaithersburg, Md.

[73] Assignee: The United States of America as represented by the Secretary of the Navy, Washington, D.C.

[21] Appl. No.: 483,687

[22] Filed: Feb. 23, 1990

[51] Int. Cl.[5] .............................................. G01N 3/32
[52] U.S. Cl. ...................................................... 73/812
[58] Field of Search .................. 73/812, 158, 828, 830

[56] References Cited

U.S. PATENT DOCUMENTS 2,291,086  7/1942  Lessig ............................... 73/812 X

OTHER PUBLICATIONS

Clark, I. E. et al., The Development of . . . Fatiguing Fibers, J. Phys. E: Sci. Instrum. vol. 12, No. 11, Nov. '79, pp. 1109–1112.

Primary Examiner—Jerry W. Myracle
Attorney, Agent, or Firm—Kenneth E. Walden; Jacob Shuster

[57] ABSTRACT

A pair of wire specimens supported within a transparent frame established by two sets of pulleys are interconnected between a common powered rotor and a pair of wire tensioning weights protectively enclosed by plastic sheathings. The wire specimens are simultaneously and cyclically displaced along direction changing paths through test medium during a testing operation terminated in response to rupture detected by sensing switches engaged by the weights.

15 Claims, 2 Drawing Sheets

FATIGUE TESTING APPARATUS

BACKGROUND OF THE INVENTION

This invention relates generally to the fatigue testing of wire by cyclic displacement under tension while immersed in a test medium.

DESCRIPTION OF PRIOR ART

Fatigue testing of wire-like specimens under tension during cyclic displacement by a motor driven pulley is generally known, as disclosed, for example, in U.S. Pat. No. 2,545,816 to Koester et al. Fatigue testing by tensioning force cyclically applied to a specimen immersed within a body of fluid, is also known as disclosed in U.S. Pat. No. 4,248,096 to Marcum.

It is an important object of the present invention to provide testing apparatus for programmed determination of the fatigue properties of different materials under different conditions to an extent not possible with prior art apparatus, and with minimal complexity.

SUMMARY OF THE INVENTION

In accordance with the present invention two wire specimens are simultaneously displaced along direction changing paths established by two sets of pulleys over which the specimens are readily installed within a transparent supporting frame through which the installation is visible. Adjacent ends of the wire specimens are operatively connected to a common rotor powered by a motor mounted by the frame in spaced relation between two containers within which test medium is retained. The wire specimens are entrained about one of the pulleys of each set carried by positioning portions of the frame projecting into the containers so as to hold the wire specimens immersed within the test medium. The remote ends of the two wire specimens are connected to wire tensioning weights protectively enclosed in plastic sheathings suspended by supporting end portions of the frame. Sensing switches mounted by the frame end portions project into the sheathings for engagement by the weights in response to rupture of the wire specimens, by means of which the testing operation is terminated and data readout obtained. Timers connected to the sensing switches and a rotation counter connected to the rotor supply the input data from which output test data is determined.

BRIEF DESCRIPTION OF THE DRAWING FIGURES

Other objects, advantages and novel features of the invention will become apparent from the following detailed description of the invention when considered in conjunction with the accompanying drawing wherein.

DETAILED DESCRIPTION OF THE PREFERRED EMBODIMENTS

Figure 1:
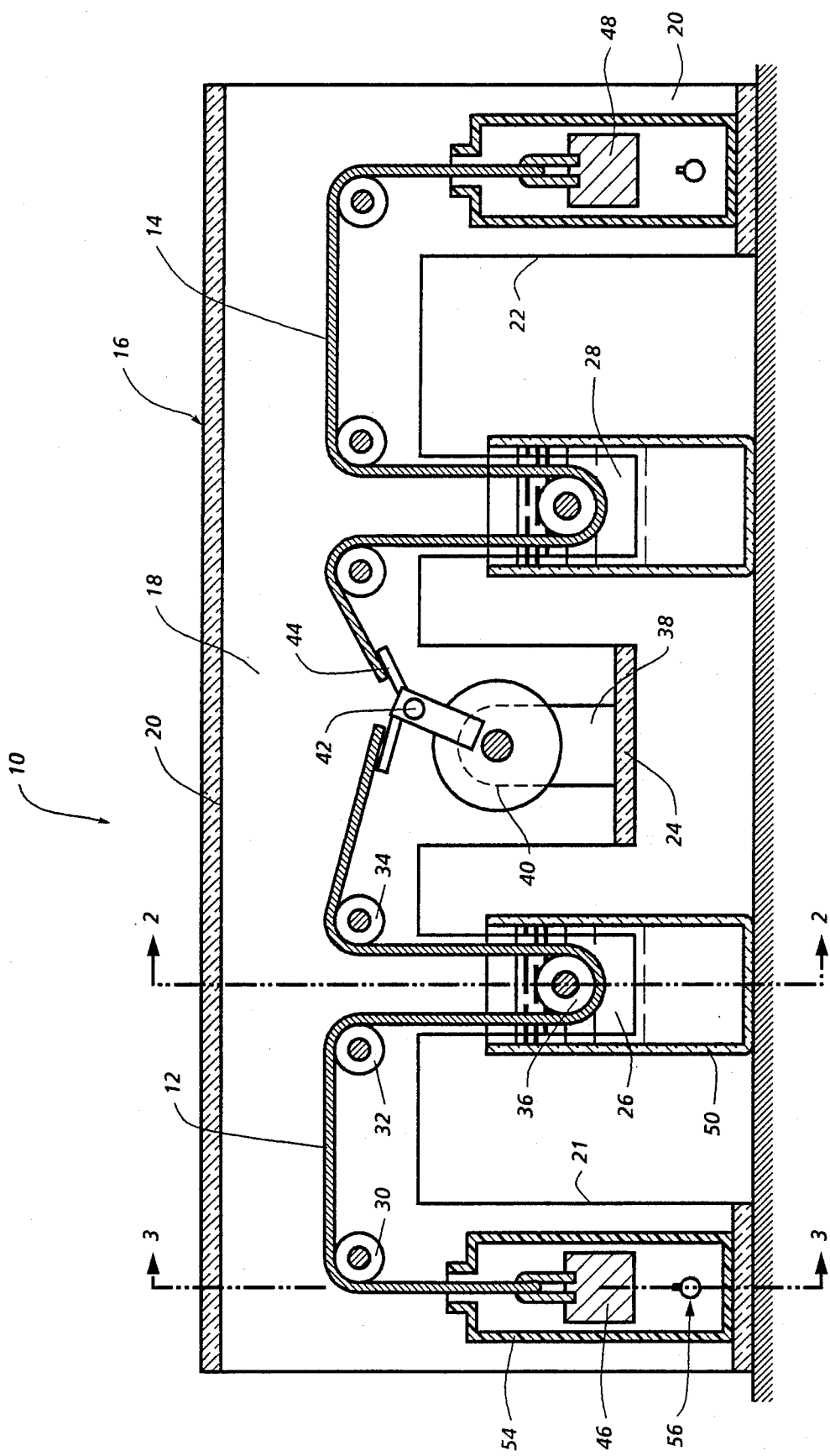
FIG. 1 is a side section view through a testing apparatus constructed in accordance with one embodiment of the invention.

Refering now to the drawing in detail, FIG. 1 illustrates testing apparatus, generally referred to by reference numeral 10, for measuring fatigue properties of materials such as amorphous alloy wire in the form of two elongated specimens 12 and 14. The specimens undergo cyclically varying strain until rupture thereof occurs to terminate the testing operation.

The specimens 12 and 14 are supported within the apparatus by a frame made of transparent Plexiglas material, generally referred to by reference numeral 16. The frame has parallel spaced side panels 18 interconnected by a top portion 20. The frame panels 18 include vertically extending support portions 21 and 22 at opposite ends, a central mounting portion 24 and a pair of positioning portions 26 and 28 spaced between the central portion 24 and the end portions 21 and 22. The wire specimens 12 and 14 are respectively supported on the frame by two sets of pulleys, each set consisting of three horizontally aligned pulley wheels 30, 32, and 34 and a pulley wheel 36 on each of the positioning portions 26 and 28 of the frame vertically spaced below the other pulley wheels. The pulley wheels 30, 32, 34, and 36 of each set establishes a direction changing path along which the wire specimens 12 and 14 extend as shown in FIG. 1.

With continued reference to FIG. 1, the central mounting portion 24 of frame mounts a motor 38, the output shaft of which is connected to a rotor disc 40. A radially extending anchor element 42 is fixed to the rotor disc, having a pivot connection 42 to a pair of nylon leads to which adjacent ends of the wire specimens 12 and 14 are fastened by epoxy glue, for example. The opposite remote ends of the wire specimens are respectively connected to tension exerting weights 46 sand 48.

Figure 2:
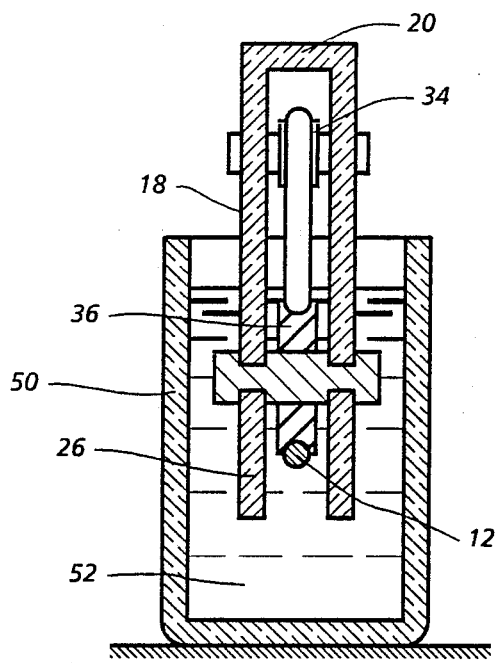
FIG. 2 is a section view taken substantially through a plane indicated by section line 2—2 in FIG. 1.

Referring now to FIGS. 1 and 2 in particular, each of the positioning portions 26 and 28 of the frame panels project into a container 50 within which a body of liquid test medium 52 is retained. The portion of the wire specimen 12 or 14 entrained about each pulley wheel 36 is thereby held immersed in the test medium 52 during cyclic displacement under tension of the weights 46 or 48. Each of such weights is guidingly enclosed within a polyethylene sheathing 54 suspended between the frame panels at end portions 21 and 22 thereof.

Figure 3:
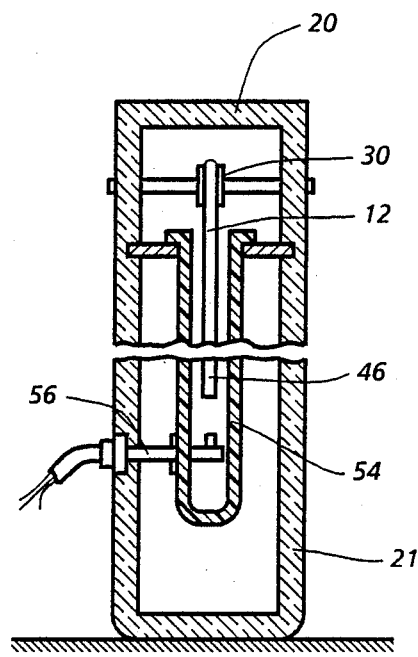
FIG. 3 is an enlarged partial section view taken substantially through a plane indicated by section line 3—3 in FIG. 1.

As more clearly seen in FIG. 3, a sensor switch device 56 mounted by the frame projects into the lower end of the sheathing 54 for engagement by the weight 46 or 48 in response to excessive vertical travel in a downward direction as a result of specimen rupture. The switch device 56 is electrically connected to a timer 58 as diagramed in FIG. 4.

Figure 4:
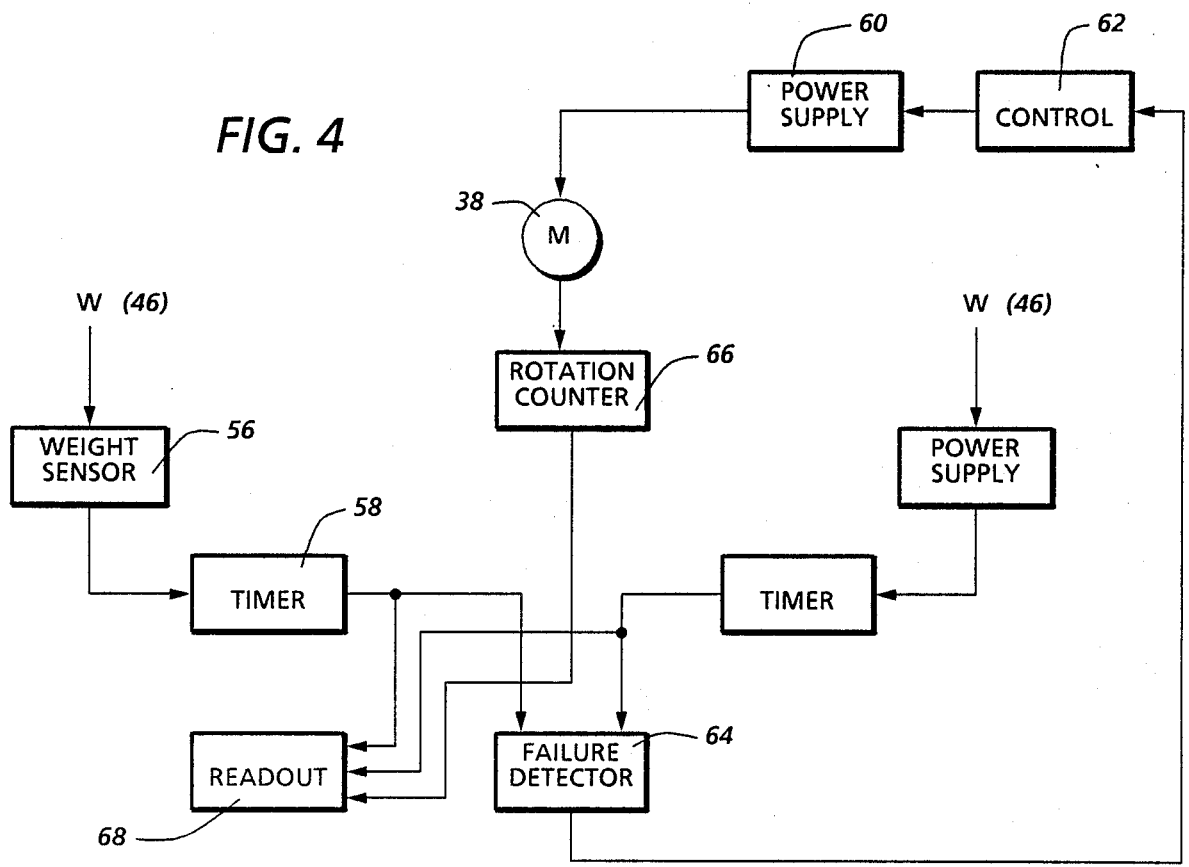
FIG. 4 is schematic block diagram of the control system associated with the apparatus shown in FIGS. 1–3.

As shown in FIG. 4, the motor 38 is energized from a suitable power supply 60 to begin a testing operation under command of a control component 62. The outputs of the aforementioned timers 58 connected to the sensors 56 associated with the weights 46 and 48, are fed to a failure detector 64 and the readout 68 to which a rotation counter 66 is also connected for obtaining fatigue property data. The detector 64 is connected to control 62 to terminate the testing operation in response to specimen rupture.

It will be apparent from the foregoing description that the two specimens 12 and 14 will undergo simultaneous cyclic displacement along the paths established by the two sets of pulley wheels 30, 32, 34 and 36, under tension of the weights 46 and 48. Further, during such testing operation each of the wire specimens will be immersed in a test medium of interest 52, retained by containers 50 at spaced locations at which the specimen paths extend about pulley wheels 36 positioned at the lower ends of the frame positioning portions 26 and 28. When rupture of the wire specimens occur, the weights 46 and 48 drop into engagement with the sensor switches 56 within the sheathings 54 to effect termination of a test operation through failure detector 64. The timers 58 and the rotation counter 66 respectively time the test operational period and count the number of reciprocatory travel cycles therein to supply inputs to the readout 68 for calculating and exhibiting fatigue property data.

The maximum strain ($\lambda$) produced in each wire specimen 12 or 14 entrained about pulley wheel 36 while immersed in the test medium 52, is determined by the diameter (d) of the wire and the effective diameter (D) of the pulley wheel 36 in accordance with the relationship: $\lambda = d/(d+D)$.

By way of example, the rotor disc 40 is rotated at a frequency of 2.0 Hz and the fatigue limit is defined as the maximum cyclic strain acheived without failure during $10^6$ cycles. The control system as diagrammed in FIG. 4 may be so programmed in connection with wire specimens of high yield strength being studied for corrosion resistance when subjected to environmental conditions reproduced in the test medium 52.

Two different material specimens under the same or different conditions may be simultaneously tested for fatigue properties by the apparatus when appropriately programmed through its control system as hereinbefore described. Further, the apparatus may be programmed for wire stretch testing to measure changes in elongation, electrical conductivity and wire diameter.

Numerous other modifications and variations of the present invention are possible in light of the foregoing teachings. It is therefore to be understood that within the scope of the appended claims the invention may be practiced otherwise than as specifically described.

What is claimed is:

1. Apparatus for fatigue testing of elongated specimens immersed within a test medium, comprising at least two containers within which said test medium is retained at locations in spaced relation to each other, a supporting frame having a pair of test positioning portions projecting into said containers, means mounted by said frame in engagement with the specimens for establishing direction changing paths along which said specimens respectively extend with the test positioning portions into the containers, motor operated means connected to said specimens for simultaneous cyclic displacement thereof along said direction changing paths through the test medium at said spaced locations thereof and means connected to said specimens for tensioning thereof during said cyclic displacement along the direction changing paths.

2. The apparatus as defiined in claim 1 wherein said supporting frame includes a pair of end portions and said tensioning means includes a pair of weights respectively connected to said specimens, means suspended by said end portions for protective enclosures of the weights during said cyclic displacement of the specimens and failure detecting means mounted by the end portions and projecting into the protective enclosure means for engagement by the weights in response to rupture of the specimens during said cyclic displacement thereof.

3. The apparatus as defined in claim 2 wherein said motor operated means includes a rotor mounted by the frame between the test positioning portions thereof and anchor means fixed to the rotor for pivotally connecting the specimens thereto.

4. The apparatus as defined in claim 3 wherein said means for establishing the direction changing paths includes pulleys mounted by the test positioning portions of the frame about which the specimens are entrained.

5. The apparatus as defined in claim 1 wherein said motor operated means includes a rotor mounted by the frame between the test positioning portions thereof and anchor means fixed to the rotor for pivotally connecting the specimens thereto.

6. The apparatus as defined in claim 1 wherein said means for establishing the direction changing paths includes pulleys mounted by the test positioning portions of the frame about which the specimens are entrained.

7. Apparatus for fatigue testing of an elongated amorphous alloy wire immersed within a test medium, comprising a container within which said test medium is retained, a supporting frame having a portion projecting into the container, motor operated means mounted by the frame in engagement with said wire for cyclic displacement thereof along said portion of the frame within the container, pulley means mounted by the frame for establishing a direction changing path along which said wire extends through the test medium within the container during said cyclic displacement thereof and means connected to said wire for tensioning thereof during said cyclic displacement.

8. Apparatus for fatigue testing of an elongated specimen immersed within a test medium, comprising a container within which said test medium is retained, a supporting frame having a portion projecting into the container, motor operated means mounted by the frame in engagement with said specimen for cyclic displacement thereof along said portion of the frame within the container, pulley means mounted by the frame for establishing a direction changing path along which said specimen extends through the test medium within the container during said cyclic displacement thereof, mean connected to said specimen for tensioning thereof during said cyclic displacement and failure detecting means responsive to rupture of said specimen for terminating operation of the motor operated means.

9. The apparatus as defined in claim 8 wherein said frame includes an end portion and means suspended by said end portion for protective enclosure of said tensioning means.

10. The apparatus as defined in claim 9 wherein said failure detecting means is mounted by the end portion of the frame and projects into the protective enclosure means.

11. The apparatus as defined in claim 10 wherein said tensioning means is a weight connected to the specimen and engageable with the failure detecting means.

12. The apparatus as defined in claim 11 wherein said specimen is amorphous alloy wire.

13. Apparatus for fatigue testing of an elongated specimen immersed within a test medium, comprising a container within which said test medium is retained, a supporting frame projecting into the container, motor operated means mounted by the frame in engagement with said specimen for cyclic displacement thereof within the container, pulley means mounted by the frame for establishing a direction changing path along which said specimen extends through the test medium within the container during said cyclic displacement thereof and means connected to said specimen for tensioning thereof during said cyclic displacement, said frame including an end portion and means suspended by said end portion for protective enclosure of said tensioning means.

14. The apparatus as defined in claim 13 wherein said frame is made of transparent material enabling visual inspection of the specimen extending along the direction changing path between the motor operated means and the tensioning means.

15. Apparatus for fatigue testing of an elongated specimen immersed within a test medium, comprising a container within which said test medium is retained, a supporting frame having a portion projecting into the container, motor operated means mounted by the frame in engagement with said specimen for cyclic displacement thereof along said portion of the frame within the container, pulley means mounted by the frame for establishing a direction changing path along which said specimen extends through the test medium within the container during said cyclic displacement thereof and means connected to said specimen for tensioning thereof during said cyclic placement, said frame being made of transparent material enabling visual inspection of the specimen extending along the direction changing path between the motor operated means and the tensioning means.

* * * * *